US011993630B2

(12) United States Patent
Falkenstein et al.

(10) Patent No.: US 11,993,630 B2
(45) Date of Patent: May 28, 2024

(54) METHOD FOR PURIFYING PEGYLATED ERYTHROPOIETIN

(71) Applicant: Hoffmann-La Roche Inc., Little Falls, NJ (US)

(72) Inventors: Roberto Falkenstein, Munich (DE); Bernhard Spensberger, Eberfing (DE)

(73) Assignee: HOFFMANN-LA ROCHE INC, Little Falls, NJ (US)

( * ) Notice: Subject to any disclaimer, the term of this patent is extended or adjusted under 35 U.S.C. 154(b) by 169 days.

(21) Appl. No.: 17/145,653

(22) Filed: Jan. 11, 2021

(65) Prior Publication Data
US 2021/0155655 A1    May 27, 2021

Related U.S. Application Data (63) Continuation of application No. 16/245,081, filed on Jan. 10, 2019, now abandoned, which is a continuation of application No. PCT/EP2017/067790, filed on Jul. 13, 2017.

(30) Foreign Application Priority Data

Jul. 15, 2016 (EP) ..................................... 16179755

(51) Int. Cl.
| | |
|---|---|
| *C07K 1/16* | (2006.01) |
| *B01D 15/26* | (2006.01) |
| *B01D 15/36* | (2006.01) |
| *C07K 1/18* | (2006.01) |
| *C07K 14/505* | (2006.01) |

(52) U.S. Cl.
CPC .............. *C07K 1/18* (2013.01); *B01D 15/362* (2013.01); *C07K 14/505* (2013.01)

(58) Field of Classification Search
None
See application file for complete search history.

(56) References Cited

U.S. PATENT DOCUMENTS

| | | | |
|---|---|---|---|
| 5,641,670 | A | 6/1997 | Treco et al. |
| 5,733,761 | A | 3/1998 | Treco et al. |
| 5,817,238 | A | 10/1998 | Makino et al. |
| 5,876,969 | A | 3/1999 | Fleer et al. |
| 5,932,462 | A | 8/1999 | Harris et al. |
| 6,583,272 | B1 | 6/2003 | Bailon |
| 10,273,277 | B2 | 4/2019 | Falkenstein et al. |
| 2002/0147311 | A1 | 10/2002 | Gillies et al. |
| 2005/0008649 | A1 | 1/2005 | Shin et al. |
| 2005/0100991 | A1 | 5/2005 | Rosen et al. |
| 2005/0114037 | A1 | 5/2005 | Desjarlais et al. |
| 2012/0197007 | A1 | 8/2012 | Falkenstein et al. |

FOREIGN PATENT DOCUMENTS

| | | |
|---|---|---|
| CN | 102056940 A | 5/2011 |
| CN | 102164954 A | 8/2011 |
| EP | 0473084 B1 | 11/1995 |
| EP | 0530447 B1 | 10/1997 |
| EP | 0442724 B1 | 10/1999 |
| EP | 1064951 B1 | 8/2007 |
| WO | 89/05157 A1 | 6/1989 |
| WO | 90/11354 A1 | 10/1990 |
| WO | 91/06667 A1 | 5/1991 |
| WO | 91/09955 A1 | 7/1991 |
| WO | 93/09222 A2 | 5/1993 |
| WO | 94/01451 A2 | 1/1994 |
| WO | 94/01451 A3 | 1/1994 |
| WO | 94/12650 A2 | 6/1994 |
| WO | 94/12650 A3 | 6/1994 |
| WO | 95/31560 A1 | 11/1995 |
| WO | 99/57134 A1 | 11/1999 |
| WO | 00/044785 A1 | 8/2000 |
| WO | 101/02017 A2 | 1/2001 |
| WO | 2004/024866 A2 | 3/2004 |
| WO | 2004/024866 A3 | 3/2004 |
| WO | 2009/010270 A2 | 1/2009 |
| WO | 2009147060 A1 | 12/2009 |
| WO | 2010034442 A1 | 4/2010 |
| WO | 2012/035037 A1 | 3/2012 |
| WO | 2018/011381 | 1/2018 |

OTHER PUBLICATIONS

US 5,733,746 A, 03/1998, Treco et al. (withdrawn)
Bristow et al. Erythropoietin BRP "Collaborative Study for the Establishment of a Biological Reference Preparation for Erythropoietin"(Bio 97-2):31-48 ( 1997).
Danielsson et al., "One-step purification of monoclonal IgG antibodies from mouse ascites" J Immunol Methods 115:79-88 ( 1988).
Delgado et al. et al., "The uses and properties of PEG-linked proteins" Crit Rev Ther Drug 9(3-4):249-304 ( 1992).
Felix, A., et al., "Site-Specific Poly(ethylene glycol)ylation of Peptides" ACCS Sym Ser 680:218-238 (Aug. 5, 1997).
Francis, G.E., et al., "PEGylation of cytokines and other therapeutic proteins and peptides: the importance of biological optimisation of coupling techniques" Int'l Journal of Hematology 68:1-18 ( 1998).
International Preliminary Report of Patentability (IPRP) for PCT/EP2017/067790 dated Jan. 15, 2019.

(Continued)

*Primary Examiner* — Elizabeth C. Kemmerer
*Assistant Examiner* — Regina M DeBerry
(74) *Attorney, Agent, or Firm* — Charles Wong (57) ABSTRACT

Herein is reported a method for the purification of a protein comprising erythropoietin and a single poly (ethylene glycol) residue from reaction by-products or not reacted starting material by a cation exchange chromatography method. It has been found that by employing a cation exchange Toyopearl® SP-650 chromatography material and employing a second wash step with an increased pH value compared to the first wash step a fusion protein of erythropoietin and a single poly (ethylene glycol) residue can be obtained in a single step with high purity and yield and suitability for large scale applications.

12 Claims, 5 Drawing Sheets

Specification includes a Sequence Listing.

(56) References Cited

OTHER PUBLICATIONS

International Search Report and Written Opinion for PCT/EP2017/067790 dated Oct. 18, 2017.

Li et al. High and New Technology of Food (English translation of the 1st paragraph and Article in Chinese),: 124-132 (2007).

Lu et al., "Pegylated peptides III. Solid-phase synthesis with pegylating reagents of varying molecular weight: synthesis of multiply pegylated peptides" Reactive Polymers 22(3):221-229 (1994).

Monfardini, C. et al., "A branched monomethoxypoly (ethylene glycol) for protein modification" Bioconjugate Chem. 6:62-69 (1995).

Morpurgo, M. et al., "Preparation and characterization of poly(ethylene glycol) vinyl sulfone" Bioconjugate Chem. 7:363-368 (1996).

Necina et al., "Capture of Human Monoclonal Antibodies from Cell Culture Supernatant by Ion Exchange Media Exhibiting High Charge Density" Biotechnology and Bioengineering 60(6):689-698 (Dec. 1998).

Schmoeger et al., "Matrix-assisted refolding of autoprotease fusion proteins on an ion exchange column" Journal of Chromatography A 1216:84608469 (2009).

Veronese, "Peptide and protein PEGylation: a review of problems and solutions" Biomaterials 22(5):405-417 (Mar. 1, 2001).

Wang et al., "High-level expression of human TFF3 in *Escherichia coli*" Peptides 26:1213-1218 (2005).

Yao et al., "Three-Dimensional Pore Structure of Chromatographic Adsorbents from Electron Tomography" Langmuir 22:11148-11157 (2006).

Yu et al., "Facile purification of mono-PEGylated interleukin-1 receptor antagonist and its characterization with mult-angle laser light scattering" Process Biochemistry 42:971-977 (2007).

Yun et al., "reproducible preparation and effective separation of PEGylated recombinant human granulocyte colony-stimulating factor with novel 'PEG-pellet' PEGylation mode and ion-exchange chromatography" Journal of Biotechnology 118:67-74 (2005).

SEQUENCE LISTING

```
<160> NUMBER OF SEQ ID NOS: 2

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 2
<211> LENGTH: 166
```

-continued

```
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

METHOD FOR PURIFYING PEGYLATED ERYTHROPOIETIN

CROSS-REFERENCE TO RELATED APPLICATIONS

This application is a Continuation of U.S. patent application Ser. No. 16/245,081, filed Jan. 10, 2019, which is a Continuation of International Patent Application No. PCT/EP2017/067790, filed Jul. 13, 2017, which claims benefit of priority to EP Patent Application No. 16179755.0 filed Jul. 15, 2016, each of which is incorporated herein by reference in its entirety.

SEQUENCE LISTING

This application contains a Sequence Listing which has been submitted electronically in ASCII format and is hereby incorporated by reference in its entirety. Said ASCII copy, created on Jan. 7, 2021, is named P33750-US-1_Sequence_Listing.txt and is 3,310 bytes in size.

Entry of the amendments to the specification is respectfully requested.

Herein is reported a method for purifying PEGylated erythropoietin with a single column process using a cation exchange chromatography material.

BACKGROUND OF THE INVENTION

Proteins play an important role in today's medical portfolio. For human application every therapeutic protein has to meet distinct criteria. To ensure the safety of biopharmaceutical agents to humans by-products accumulating during the production process have to be removed especially. To fulfill the regulatory specifications one or more purification steps have to follow the manufacturing process. Among other things, purity, throughput, and yield play an important role in determining an appropriate purification process.

Conjugates of therapeutic proteins have been reported, for example, for polyethylene glycol (PEG) and Interleukin-6 (EP 0 442 724), for PEG and erythropoietin (WO 01/02017), for chimeric molecules comprising Endostatin and immunoglobulins (US 2005/008649), for secreted antibody based fusion proteins (US 2002/147311), for fusion polypeptides comprising albumin (US 2005/0100991; human serum albumin U.S. Pat. No. 5,876,969), for PEGylated polypeptides (US 2005/0114037), and for erythropoietin fusions.

Necina, R., et al. (Biotechnol. Bioeng. 60 (1998) 689-698) reported the capture of human monoclonal antibodies directly from cell culture supernatants by ion exchange media exhibiting high charge density. In WO 89/05157 a method is reported for the purification of product immunoglobulins by directly subjecting the cell culture medium to a cation exchange treatment. A one-step purification of monoclonal IgG antibodies from mouse ascites is described by Danielsson, A., et al., J. Immun. Meth. 115 (1988) 79-88. A method for purifying a polypeptide by ion exchange chromatography is reported in WO 2004/024866 in which a gradient wash is used to resolve a polypeptide of interest from one or more contaminants. In EP 0 530 447 a process for purifying IgG monoclonal antibodies by a combination of three chromatographic steps is reported. A facile purification of mono-PEGylated interleukin-1 receptor antagonist is reported by Yu, G., et al., Process Biotechnol. 42 (2007) 971-977. Wang, H., et al., Peptides 26 (2005) 1213-1218; reports the purification of hTFF3 expressed in *E. coli* by a two step cation exchange chromatography. Yun, Q., et al. (Yun, Q., et al., J. Biotechnol. 118 (2005) 67-74) report the purification of PEGylated rhG-CSF by two consecutive ion-exchange chromatography steps.

A method for purifying PEGylated erythropoietin on a SP Sephacryl S 500 HR column is reported in WO 2012/035037.

WO 1999/057134 reports for protein purification by ion exchange chromatography.

A method for the purification of mono-PEGylated erythropoietin comprising two cation exchange chromatography steps wherein the same type of cation exchange material is used in both cation exchange chromatography steps is reported in WO 2009/010270.

SUMMARY OF THE INVENTION

Herein is reported a method for the purification of a protein conjugate comprising erythropoietin and a single poly (ethylene glycol) residue from reaction by-products or not reacted starting material by a cation exchange chromatography method.

It has been found that by employing a wash step with a washing solution with increased pH value the conjugated protein comprising erythropoietin and a single poly (ethylene glycol) residue can be obtained from a cation exchange chromatography material, such as for example Toyopearl® SP-650, in a single step with high purity and yield in an improved and simplified way.

It has been found that when compared to a purification process for a protein conjugate comprising erythropoietin and a single poly (ethylene glycol) residue that employs two sequential cation exchange chromatography steps, the yield and the quality are at least comparable or better. The one column process allows for obtaining the same quality while increasing the robustness of the process. It also reduces the manufacturing costs and production time. Final yields can be increased without loss of quality of the mono-PEGylated erythropoietin.

Thus, herein is reported as one aspect a method for obtaining/purifying/producing a protein, which comprises erythropoietin and a single poly (ethylene glycol) residue, comprising the following steps:
 a) applying a solution comprising a mixture of erythropoietin and conjugates of erythropoietin and poly (ethylene glycol) with one or more poly (ethylene glycol) residues per erythropoietin molecule to a column, comprising Toyopearl® SP-650 as chromatography material, to which a first solution with a pH of about 2.4 to about 2.7 has been applied,
 b) applying a second solution with an increased pH value with respect to the first solution (with a pH of about 2.4 to about 2.7),
 c) applying a solution with increased or increasing conductivity to the column and thereby recovering the protein, which comprises erythropoietin and a single poly (ethylene glycol) residue.

Herein is reported as one aspect a method for obtaining/purifying/producing a protein, which comprises erythropoietin and a single poly (ethylene glycol) residue, comprising the following steps:
 a) applying a solution comprising a mixture of erythropoietin and conjugates of erythropoietin and poly (ethylene glycol) with one or more poly (ethylene glycol) residues per erythropoietin molecule to a column, comprising a chromatography material that has a matrix of methacrylate with a sulfopropyl as functional group, to which a first solution with a pH of about 2.4 to about 2.7 has been applied, b) applying a second solution with an increased pH value with respect to the first solution (with a pH of about 2.4 to about 2.7), c) applying a solution with increased or increasing conductivity to the column and thereby recovering the protein, which comprises erythropoietin and a single poly (ethylene glycol) residue.

In one embodiment the method further comprises the step of re-applying the first solution with a pH of about 2.4 to about 2.7 after step b) and before step c). Thus, in one embodiment is reported a method for obtaining/purifying/producing a protein, which comprises erythropoietin and a single poly (ethylene glycol) residue, comprising the following steps:

a) applying a solution comprising a mixture of erythropoietin and conjugates of erythropoietin and poly (ethylene glycol) with one or more poly (ethylene glycol) residues per erythropoietin molecule to a column, comprising Toyopearl® SP-650 chromatography material, to which a first solution with a pH of about 2.4 to about 2.7 has been applied, b) applying a second solution with an increased pH value with respect to the first solution with a pH of about 2.4 to about 2.7, b1) re-applying the first solution with a pH of about 2.4 to about 2.7, c) applying a solution with increased or increasing conductivity to the column and thereby recovering the protein, which comprises erythropoietin and a single poly (ethylene glycol) residue.

In one embodiment the second solution with an increased pH value is a solution with a pH of about 2.7 to about 3.2, preferably with a pH of about 2.7 to 3.0.

In one embodiment the second solution with an increased pH value is a solution with a constant conductivity value.

In one embodiment the second solution with an increased pH value and the first solution with a pH of about 2.4 to about 2.7 have about the same, constant conductivity value.

In one embodiment the second solution with an increased pH value and/or the first solution with a pH of about 2.4 to about 2.7 have a constant conductivity value of about 19 mS/cm, preferably with a conductivity value of about 17 mS/cm to about 19 mS/cm.

In one embodiment the second solution with an increased pH value has a pH of about 2.7 to about 3.2 and has a conductivity value of about 19 mS/cm.

In one embodiment the second solution with an increased pH value is a phosphate buffered solution.

In one embodiment the solution comprising a mixture of erythropoietin and conjugates of erythropoietin and poly (ethylene glycol) with one or more poly (ethylene glycol) residues per erythropoietin molecule is not adjusted to a conductivity value of about 19 mS/cm.

In one embodiment the solution with increased or increasing conductivity is a solution with increased or increasing sodium chloride concentration. In one embodiment the solution with increased or increasing conductivity has a pH value of from pH 2.3 to pH 3.5.

In one embodiment the solution with increased or increasing conductivity has a conductivity that increases step-wise or linearly.

In one embodiment the method is used in large scale protein preparations wherein the chromatography column of step a) has a diameter of at least 30 cm.

In one embodiment the erythropoietin is human erythropoietin. In one embodiment the human erythropoietin has the amino acid sequence of SEQ ID NO: 01 or SEQ ID NO: 02.

In one embodiment the single poly (ethylene glycol) residue has a molecular weight of from 20 kDa to 40 kDa.

Herein is reported in one aspect a method for obtaining a protein, which comprises erythropoietin and a single poly (ethylene glycol) residue, comprising the following steps:

a) applying a solution comprising a mixture of erythropoietin and conjugates of erythropoietin and poly (ethylene glycol) with one or more poly (ethylene glycol) residues per erythropoietin molecule to a column, comprising Toyopearl® SP-650 M as chromatography material, to which a first solution with a pH of about 2.4 to about 2.7 has been applied, a1) re-applying the first solution with a pH of about 2.4 to about 2.7, b) applying a second solution with an increased pH value with respect to the first solution with a pH of about 2.4 to about 2.7, c) applying a solution with increased or increasing conductivity to the column and thereby recovering the protein, which comprises erythropoietin and a single poly (ethylene glycol) residue.

DESCRIPTION OF THE INVENTION

Herein is reported a method for purifying a protein, which comprises one erythropoietin molecule and one poly (ethylene glycol) residue, with a gradient elution method on a cation exchange chromatography column, such as for example a column comprising Toyopearl® SP-650, whereby the cation exchange chromatography/Toyopearl® SP-650 column has been washed with two washing solutions prior to starting the recovering/elution of the protein, which comprises one erythropoietin molecule and one poly (ethylene glycol) residue. Herein, the second washing solution has an increased pH value with respect to the first washing solution.

General chromatographic methods and their use are known to a person skilled in the art. See for example, Heftmann, E., (ed.), Chromatography, 5$^{th}$ edition, Part A: Fundamentals and Techniques, Elsevier Science Publishing Company, New York (1992); Deyl, Z., (ed.), Advanced Chromatographic and Electromigration Methods in Biosciences, Elsevier Science BV, Amsterdam, The Netherlands (1998); Poole, C. F., and Poole, S. K., Chromatography Today, Elsevier Science Publishing Company, New York (1991); Scopes, Protein Purification: Principles and Practice, Springer Verlag (1982); Sambrook, J., et al., (eds.), Molecular Cloning: A Laboratory Manual, Second Edition, Cold Spring Harbor Laboratory Press, Cold Spring Harbor, N.Y., (1989); or Ausubel, F. M., et al., (eds.), Current Protocols in Molecular Biology, John Wiley & Sons, Inc., New York (1987-1994).

The term "applying to" denotes a partial step of a purification method in which a solution is brought in contact with a chromatography material. This denotes that either a) the solution is added to a chromatographic device in which the chromatography material is contained, or b) that the chromatography material is added to the solution. In case a) the solution passes through the device allowing for an interaction between the chromatography material and the substances contained in the solution. Depending on the conditions, such as e.g. pH, conductivity, salt concentration, temperature, and/or flow rate, some substances of the solution bind to the chromatography material and, thus, can be recovered from the chromatography material in a further step. The substances remaining in solution can be found in the flow-through. The "flow-through" denotes the solution obtained after the passage of the device, which may either be the applied solution or a buffered solution, which is used to wash the column or to cause elution of substances bound to the chromatography material. In one embodiment the device is a column or a cassette. In case b) the chromatography material can be added, e.g. as a solid, to the solution, e.g. containing the substance of interest to be purified, allowing for an interaction between the chromatography material and the substances in solution. After the interaction the chromatography material is removed, e.g. by filtration, and substance bound to the chromatography material are also removed therewith from the solution, whereas substances not bound to the chromatography material remain in solution.

The term "bind-and-elute mode" denotes an operation mode of a chromatography step, in which a solution containing a substance of interest to be purified is applied to a chromatography material, whereby the substance of interest binds to the chromatography material. Thus, the substance of interest is retained on the chromatography material, whereas substances not of interest are removed with the flow-through or the supernatant. The substance of interest is afterwards recovered from the chromatography material in a second step with an elution solution. In one embodiment the method as reported herein is operated in bind-and-elute mode.

The solutions employed in the method as reported herein are crude or buffered solutions. The term "buffered solution" denotes a solution in which changes of pH due to the addition or release of acidic or alkaline substances is leveled by the dissolved buffer substance. Any buffer substance with such properties can be used. Generally pharmaceutically acceptable buffer substances are used. In one embodiment the buffered solution is selected from a phosphate buffered solution consisting of phosphoric acid and/or salts thereof, or an acetate buffered solution consisting of acetic acid and salts thereof, or a citrate buffered solution consisting of citric acid and/or salts thereof, or a morpholine buffered solution, or a 2-(N-morpholino) ethanesulfonic buffered solution, or a histidine buffered solution, or a glycine buffered solution, or a tris (hydroxymethyl) aminomethane (TRIS) buffered solution. In one embodiment the buffered solution is selected from a phosphate buffered solution, or an acetate buffered solution, or a citrate buffered solution, or a histidine buffered solution. Optionally the buffered solution may comprise an additional salt, such as e.g. sodium chloride, sodium sulphate, potassium chloride, potassium sulfate, sodium citrate, or potassium citrate. It is understood in the art that buffered solutions are prepared under conditions comparable to those in which they are later used. For example, the pH of a buffered solution is adjusted at a temperature that is comparable to a temperature at which the solution is later used in the intended process. If, for example a buffered solution is used in a chromatography method that is performed at 4° C., the pH would be adjusted when the buffered solution has a comparable temperature and e.g. not at 30° C. In one embodiment the second solution with an increased pH value is a phosphate buffered solution.

The terms "continuous elution" and "continuous elution method", which are used interchangeably within this application, denote a method wherein the conductivity of a solution causing elution, i.e. the recovery of a bound compound from a chromatography material, is changed, i.e. raised or lowered, continuously, i.e. the concentration is changed by a sequence of small steps each not bigger than a change of 2%, or of 1% of the concentration of the substance causing elution. In this "continuous elution" one or more conditions, for example the pH, the ionic strength, concentration of a salt, and/or the flow of a chromatography, may be changed linearly or exponentially or asymptotically. In one embodiment the change is linear.

The terms "step elution", "step-wise elution", "step-wise elution method" and "step elution method", which are used interchangeably within this application, denote a method wherein e.g. the concentration of a substance causing elution, i.e. the dissolution of a bound compound from a material, is raised or lowered at once, i.e. directly from one value/level to the next value/level. In this "step elution" one or more conditions, for example the pH, the ionic strength, concentration of a salt, and/or the flow of a chromatography, is/are changed all at once from a first, e.g. starting, value to a second, e.g. final, value, i.e. the conditions are changed incrementally, i.e. stepwise, in contrast to a linear change. In the "step elution method" is after each increase in the ionic strength a new fraction collected. This fraction contains the compounds recovered from the ion exchange material with the corresponding increase in ionic strength. After each increase the conditions are maintained till the next step in the elution method. In the "step elution" one or more conditions is/are changed all at once from a first, e.g. starting, value to a second, e.g. final, value. The change can be 10% or more of the concentration of the substance causing elution. That is in case the concentration of the substance causing elution is 100% in the first step, 110% or more in the second step, and 120% or more in the third step. Also the change can be 50% or more of the concentration of the substance causing elution. Further, the change can be 120% or more of the concentration of the substance causing elution. "Step elution" denotes that the conditions are changed incrementally, i.e. stepwise, in contrast to a linear change.

The term "ion exchange chromatography material" denotes an immobile high molecular weight matrix that carries covalently bound charged substituents used as stationary phase in ion exchange chromatography. For overall charge neutrality not covalently bound counter ions are bound thereto. The "ion exchange chromatography material" has the ability to exchange its not covalently bound counter ions for similarly charged ions of the surrounding solution. Depending on the charge of its exchangeable counter ions the "ion exchange resin" is referred to as cation exchange resin or as anion exchange resin. Depending on the nature of the charged group (substituent) the "ion exchange resin" is referred to as, e.g. in the case of cation exchange resins, sulfonic acid resin (S), or sulfopropyl resin (SP), or carboxymethyl resin (CM). Depending on the chemical nature of the charged group/substituent the "ion exchange resin" can additionally be classified as strong or weak ion exchange resin, depending on the strength of the covalently bound charged substituent. For example, strong cation exchange resins have a sulfonic acid group, preferably a sulfopropyl group, as charged substituent, weak cation exchange resins have a carboxylic group, preferably a carboxymethyl group, as charged substituent, and weak anion exchange resins have a diethylaminoethyl group as charged substituent. In one embodiment the cation exchange chromatography material is a strong cation exchange chromatography material. In one embodiment the cation exchange chromatography material is a Toyopearl® SP-650 chromatography material. In one embodiment the cation exchange chromatography material is Toyopearl® SP-650 M chromatography material.

To a person skilled in the art procedures and methods are well known to convert an amino acid sequence, e.g. of a polypeptide, into a corresponding nucleic acid sequence encoding this amino acid sequence. Therefore, a nucleic acid is characterized by its nucleic acid sequence consisting of individual nucleotides and likewise by the amino acid sequence of a polypeptide encoded thereby.

The term "poly (ethylene glycol)" or "poly (ethylene glycol) residue" denotes a non-proteinaceous residue containing poly (ethylene glycol) as essential part. Such a poly (ethylene glycol) residue can contain further chemical groups which are necessary for binding reactions, which results from the chemical synthesis of the molecule, or which is a spacer for optimal distance of parts of the molecule. These further chemical groups are not used for the calculation of the molecular weight of the poly (ethylene glycol) residue. In addition, such a poly (ethylene glycol) residue can consist of one or more poly (ethylene glycol) chains which are covalently linked together. Poly (ethylene glycol) residues with more than one PEG chain are called multiarmed or branched poly (ethylene glycol) residues. Branched poly (ethylene glycol) residues can be prepared, for example, by the addition of polyethylene oxide to various polyols, including glycerol, pentaerythriol, and sorbitol. Branched poly (ethylene glycol) residues are reported in, for example, EP 0 473 084, U.S. Pat. No. 5,932,462. In one embodiment the poly (ethylene glycol) residue has a molecular weight of 20 kDa to 35 kDa and is a linear poly (ethylene glycol) residue. In another embodiment the poly (ethylene glycol) residue is a branched poly (ethylene glycol) residue with a molecular weight of 35 kDa to 40 kDa.

The term "fusion of erythropoietin with a poly (ethylene glycol) residue" denotes a covalent chemically introduced linkage of a poly (ethylene glycol) residue at the N-terminus or an internal lysine residue of erythropoietin. The fusion results in a protein conjugate, which comprises one erythropoietin molecule and one or more poly (ethylene glycol) residue/residues. The fusion process is also denoted as PEGylation and the product thereof as PEGylated erythropoietin. The fusion/conjugation of polypeptides with poly (ethylene glycol) residues is widely known in the state of the art and reviewed by, for example, Veronese, F. M., Biomaterials 22 (2001) 405-417. The poly (ethylene glycol) residue can be linked using different functional groups. Poly (ethylene glycols) with different molecular weight, different form, as well as different linking groups can be used (see also Francis, G. E., et al., Int. J. Hematol. 68 (1998) 1-18; Delgado, C., et al., Crit. Rev. Ther. Drug Carrier Systems 9 (1992) 249-304). The fusion of erythropoietin and a poly (ethylene glycol) residue can be performed in aqueous solution with poly (ethylene glycol) residue reagents as described, for example, in WO 00/44785. The fusion can also be performed at the solid phase according to Lu, Y., et al., Reactive Polymers 22 (1994) 221-229. Not randomly, N-terminally fusion can also be produced according to WO 94/01451.

The terms "fusing erythropoietin and poly (ethylene glycol)" and "PEGylation" denote the formation of a covalent linkage between a poly (ethylene glycol) residue at the N-terminus of the erythropoietin and/or an internal lysine residue in order to obtain a protein conjugate, which comprises one erythropoietin molecule and one poly (ethylene glycol) residue. In one embodiment PEGylation of erythropoietin is performed in aqueous solution using NHS-activated linear or branched PEG molecules of a molecular weight between 5 kDa and 40 kDa.

The term "under conditions suitable for binding" and grammatical equivalents thereof as used within this application denotes that a substance of interest, e.g. PEGylated erythropoietin, binds to a stationary phase when brought in contact with it, e.g. an ion exchange material. This does not necessarily denote that 100% of the substance of interest is bound but essentially 100% of the substance of interest is bound, i.e. at least 50% of the substance of interest is bound, at least 75% of the substance of interest is bound, at least 85% of the substance of interest is bound, or more than 95% of the substance of interest is bound to the stationary phase.

The chemical fusion or conjugation of erythropoietin and poly (ethylene glycol) generally results in a mixture of different compounds, such as poly-PEGylated erythropoietin (oligo-PEGylated erythropoietin), mono-PEGylated erythropoietin (with a single poly (ethylene glycol) residue), not-PEGylated erythropoietin, hydrolysis products of the activated PEG ester, as well as hydrolysis products of the erythropoietin itself. In order to obtain a mono-PEGylated erythropoietin in substantially homogeneous form these substances have to be removed/separated from each other.

Therefore, it is one aspect as reported herein to provide a method for obtaining a protein, which comprises erythropoietin and a single poly (ethylene glycol) residue, comprising the following steps:

a) applying a solution comprising a mixture of erythropoietin and conjugates of erythropoietin and poly (ethylene glycol) with one or more poly (ethylene glycol) residues per erythropoietin molecule to a column, comprising a cation exchange chromatography material, to which a first solution with a pH of about 2.4 to about 2.7 has been applied, b) applying a second solution with an increased pH value with respect to the first solution with a pH of about 2.4 to about 2.7, c) applying a solution with increasing conductivity to the column and thereby recovering separately the protein, which comprises erythropoietin and a single poly (ethylene glycol) residue, and erythropoietin, whereby the protein comprising erythropoietin and a single poly (ethylene glycol) residue is recovered first.

In one embodiment the cation exchange chromatography material is a strong cation exchange chromatography material. In one embodiment the cation exchange chromatography material is a Toyopearl® SP-650 chromatography material. In one embodiment the cation exchange chromatography material is Toyopearl® SP-650 M chromatography material.

In one embodiment the second solution with an increased pH value is a solution with a constant conductivity value. In one embodiment the second solution with an increased pH value and/or the first solution with a pH of about 2.4 to about 2.7 have a constant conductivity value of about 17 mS/cm to about 19 mS/cm. In one embodiment the second solution with an increased pH value has a pH of about 2.7 to about 3.0 and has a conductivity value of about 17 mS/cm to about 19 mS/cm.

In one embodiment the second solution with an increased pH value has a pH of about 2.7 to about 3.2 and has a conductivity value of about 17 mS/cm to about 19 mS/cm.

In one embodiment the second solution with an increased pH value has a pH of about 2.7 to about 3.0 and has a conductivity value of about 17 mS/cm to about 19 mS/cm.

In one preferred embodiment the second solution with an increased pH value has a pH of about 2.7 to about 2.9 and has a conductivity value of about 17 mS/cm to about 19 mS/cm or a pH of about 2.7 to about 3.0 and a conductivity value of about 17 mS/cm to about 18 mS/cm.

In one embodiment the second solution with an increased pH value and the first solution with a pH of about 2.4 to about 2.7 have about the same, constant conductivity value.

In one embodiment the cation exchange chromatography material has a matrix of methacrylate with a sulfopropyl as functional group. In one embodiment the cation exchange chromatography material has a particle size of about 65 μm.

This method is especially useful for the purification of PEGylated recombinant erythropoietin, which is glycosylated, i.e. which has been produced by a mammalian cell, in one embodiment by a CHO cell, or a HEK293 cell, or a BHK cell, or a Per. C6® cell, or a HeLa cell and is afterwards chemically PEGylated.

In the first step of the method the erythropoietin is PEGylated. The poly (ethylene glycol) (PEG) polymer molecules used in the PEGylation reaction have a molecular weight of about 20 kDa to 40 kDa (the term "molecular weight" as used herein is to be understood as the mean molecular weight of the PEG because PEG as polymeric compound is not obtained with a defined molecular weight but in fact has a molecular weight distribution; the term "about" indicates that in the PEG preparations, some molecules will weigh more and some less than the indicated molecular weight, i.e the term about refers to a molecular weight distribution in which 95% of the PEG molecules have a molecular weight within +/−10% of the indicated molecular weight. For example, a molecular weight of 30 kDa denotes a range of from 27 kDa to 33 kDa).

The term "erythropoietin" and its abbreviation "EPO" refer to a protein having the amino acid sequence of SEQ ID NO: 1 or of SEQ ID NO: 2, or a protein or polypeptide substantially homologous thereto, whose biological properties relate to the stimulation of red blood cell production and the stimulation of the division and differentiation of committed erythroid progenitors in the bone marrow. Recombinant erythropoietin may be prepared via expression in eukaryotic cells, for example in CHO cells, or BHK cells, or HeLa cells by recombinant DNA technology or by endogenous gene activation, i.e. the erythropoietin glycoprotein is expressed by endogenous gene activation, see for example U.S. Pat. Nos. 5,733,761, 5,641,670, U.S. Pat. No. 5,733,746, WO 93/09222, WO 94/12650, WO 95/31560, WO 90/11354, WO 91/06667, and WO 91/09955. In one embodiment the erythropoietin is human EPO. In one embodiment the human erythropoietin has the amino acid sequence set out in SEQ ID NO: 1 or SEQ ID NO: 2. In one embodiment the human erythropoietin has the amino acid sequence set out in SEQ ID NO: 1. The term "erythropoietin" also denotes variants of the protein of SEQ ID NO: 1 or of SEQ ID NO: 2, in which one or more amino acid residues have been changed, deleted, or inserted, and which has comparable biological activity as the not modified protein, such as e.g. reported in EP 1 064 951 or U.S. Pat. No. 6,583,272. A variant may have the amino acid sequence of human erythropoietin having from 1 to 6 additional sites for glycosylation. The specific activity of PEGylated erythropoietin can be determined by various assays known in the art. The biological activity of the purified PEGylated erythropoietin are such that administration of the protein by injection to human patients results in bone marrow cells increasing production of reticulocytes and red blood cells compared to non-injected or control groups of subjects. The biological activity of the PEGylated erythropoietin obtained and purified in accordance with the method as reported herein can be tested by methods according to Bristow, A., Pharmeuropa Spec. Issue Biologicals BRP Erythropoietin Bio 97-2 (1997) 31-48.

Amino acid sequence variants of erythropoietin can be prepared by introducing appropriate modifications into the nucleotide sequence encoding the erythropoietin, or by peptide synthesis. Such modifications include, for example, deletions from, and/or insertions into, and/or substitutions of residues within the amino acid sequences of the erythropoietin. Any combination of deletion, insertion, and substitution can be made to arrive at the final construct, provided that the final construct possesses comparable biological activity to the human erythropoietin.

Conservative amino acid substitutions are shown in Table 1 under the heading of "preferred substitutions". More substantial changes are provided in Table 1 under the heading of "exemplary substitutions", and as described below in reference to amino acid side chain classes. Amino acid substitutions may be introduced into human erythropoietin and the products screened for retention of the biological activity of human erythropoietin.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The chemical PEGylation of erythropoietin generally result in a protein preparation comprising erythropoietin which is PEGylated at one or more ε-amino groups of lysine residues and/or at the N-terminal amino group. Selective PEGylation at the N-terminal amino acid can be performed according to Felix, A. M., et al., ACS Symp. Ser. 680 (Poly(ethylene glycol)) (1997) 218-238. Selective N-terminal PEGylation can be achieved during solid-phase synthesis by coupling of a $N^\alpha$-PEGylated amino acid derivative to the N−1 terminal amino acid of the peptide chain. Side chain PEGylation can be performed during solid-phase synthesis by coupling of $N^\epsilon$-PEGylated lysine derivatives to the growing chain. Combined N-terminal and side chain PEGylation is feasible either as described above within solid-phase synthesis or by solution phase synthesis by applying activated PEG reagents to an amino deprotected peptide.

Suitable PEG derivatives are activated PEG molecules with as in one embodiment an average molecular weight of from about 5 kDa to about 40 kDa, in another embodiment of from about 20 kDa to about 40 kDa, and in a further embodiment of about 30 kDa to about 35 kDa. The PEG derivatives can be linear or branched PEGs. A wide variety of PEG derivatives suitable for use in the preparation of PEG-protein and PEG-peptide conjugates are available.

Activated PEG derivatives are known in the art and are described in, for example, Morpurgo, M., et al., J. Bioconjug. Chem. 7 (1996) 363-368, for PEG-vinylsulfone. Linear chain and branched chain PEG species are suitable for the preparation of the PEGylated fragments. Examples of reactive PEG reagents are iodo-acetyl-methoxy-PEG, or methoxy-PEG-vinylsulfone (m is in one embodiment an integer from about 450 to about 900 and R is lower alkyl, linear or branched, having one to six carbon atoms such as methyl, ethyl, isopropyl, etc. whereby methyl is preferred):

The use of these iodo-activated substances is known in the art and described e.g. by Hermanson, G. T., in Bioconjugate Techniques, Academic Press, San Diego (1996) pp. 147-148.

In one embodiment the PEG species is an activated PEG ester, e.g., N-hydroxysuccinimidyl propionate, or N-hydroxysuccinimidyl butanoate, or N-hydroxysuccinimide such as PEG-NHS (Monfardini, C., et al., Bioconjugate Chem. 6 (1995) 62-69). In one embodiment the PEG is activated by N-hydroxysuccinimide ester using alkoxy-PEG-N-hydroxysuccinimide, such as methoxy-PEG-N-hydroxysuccinimide (MW 30000), wherein R and m are as defined above. In one embodiment the PEG species is the N-hydroxysuccinimidyl ester of methoxy poly (ethylene glycol)-butyric acid. The term "alkoxy" refers to an alkyl ether group in which the term 'alkyl' means a straight-chain or branched-chain alkyl group containing a maximum of four carbon atoms, such as methoxy, ethoxy, n-propoxy and the like, preferably methoxy.

The term "substantially homogeneous form" denotes that the erythropoietin protein fusion or conjugate obtained, contained, or used is one having a defined number of PEG residues attached. In one embodiment the PEGylated erythropoietin is a mono-PEGylated erythropoietin. The preparation may contain unreacted (i.e., PEG group lacking) erythropoietin, poly-PEGylated erythropoietin, as well as fragments of the polypeptide generated during the PEGylation reaction. The term "substantially homogeneous form" denotes that a preparation of a mono-PEGylated erythropoietin contains at least 50% (w/w) of the mono-PEGylated erythropoietin, or at least 75% of the mono-PEGylated erythropoietin, or at least 90% of the mono-PEGylated erythropoietin, or more than 95% of the mono-PEGylated erythropoietin. The percent values are based on the area-% of the chromatogram corresponding to the chromatography method with which the mono-PEGylated erythropoietin is obtained.

Herein is reported a method for the purification of a PEGylated erythropoietin in order to obtain a substantially homogeneous form of a mono-PEGylated erythropoietin. It has been found that the purification process can be improved using/employing only a single chromatography step resulting in a process which is simplified and technically more practicable.

Therefore the current invention provides a method for the obtaining/producing/purifying mono-PEGylated erythropoietin using a Toyopearl® SP-650 chromatography material in a single chromatography step by introducing/applying a wash step in addition to the normal wash step, which employs a solution that has pH value that is increased with respect to the pH value in the first wash step. If has been found that the removal/reduction of impurities of oligo-PEGylated erythropoietin in the mono-PEGylated erythropoietin can be improved by using this additional wash step.

Therefore, the method for obtaining/producing/purifying a protein, which comprises erythropoietin and a single poly (ethylene glycol) residue, as reported herein comprises the following steps:
a) applying a solution comprising a mixture of erythropoietin and conjugates of erythropoietin and poly (ethylene glycol) with one or more poly (ethylene glycol) residues per erythropoietin molecule to a column, comprising Toyopearl® SP-650 as chromatography material, to which a first solution with a pH of about 2.4 to about 2.7 has been applied,
b) applying a second solution with an increased pH value with respect to the first solution with a pH of about 2.4 to about 2.7,
c) applying a solution with increasing conductivity to the column and thereby recovering the protein, which comprises erythropoietin and a single poly (ethylene glycol) residue.

It has been found that the separation of mono-PEGylated erythropoietin from/removal of by-products is improved if after applying the wash solution with the increased pH, the first wash solution with the lower pH is re-applied. Thus, in one embodiment the method further comprises the step of re-applying the first solution with a pH of about 2.4 to about 2.7 after step b) and before step c).

It has been found that in the additional/second wash step the second solution should have an increased pH value, whereby the increase is by a certain magnitude.

In one embodiment the pH of the second solution with an increased pH value is a solution with a pH of about 2.7 to about 3.1. In one preferred embodiment the pH of the second solution with an increased pH value is a solution with a pH of about 2.7 to about 3.0. In one preferred embodiment the pH of the second solution with an increased pH value is a solution with a pH of about 2.7 to about 2.9. In one embodiment the pH of the second solution with an increased pH value is a solution with a pH of about 2.8 to about 3.0.

In one embodiment the pH of the second solution with an increased pH value is increased by up to 25% compared to the first solution. In one embodiment the pH of the second solution with an increased pH value is increased by up to 20% compared to the first solution. In one embodiment the pH of the second solution with an increased pH value is increased by up to 15% compared to the first solution.

In one embodiment the pH of the second solution with an increased pH value is increased by 0.5 pH units compared to the first solution. In one embodiment the pH of the second solution with an increased pH value is increased by 0.4 pH units compared to the first solution. In one embodiment the pH of the second solution with an increased pH value is increased by 0.3 pH units compared to the first solution. In one embodiment the pH of the second solution with an increased pH value is increased by 0.2 pH units compared to the first solution. In one embodiment the pH of the second solution with an increased pH value is increased by 0.1 pH units compared to the first solution.

In one embodiment the pH of the second solution with an increased pH value is increased by 0.1 to 0.5 pH units compared to the first solution. In one embodiment the pH of the second solution with an increased pH value is increased by 0.3 to 0.5 pH units compared to the first solution.

The solution with an increased pH value should be applied as a solution with constant conductivity, i.e. at a conductivity value that varies by at most +/−10%, preferably by at most +/−5%.

In one embodiment the second solution with an increased pH value is a solution with a constant conductivity value. In one embodiment the second solution with an increased pH value and/or the first solution with a pH of about 2.4 to about 2.7 have a constant conductivity value of about 17 mS/cm. In one embodiment the second solution with an increased pH value and/or the first solution with a pH of about 2.4 to about 2.7 have a constant conductivity value of about 18 mS/cm. In one embodiment the second solution with an increased pH value and/or the first solution with a pH of about 2.4 to about 2.7 have a constant conductivity value of about 19 mS/cm. In one embodiment the second solution with an increased pH value has a pH of about 2.7 to about 3.0 and has a conductivity value of about 17 mS/cm. In one embodiment the second solution with an increased pH value has a pH of about 2.7 to about 3.0 and has a conductivity value of about 18 mS/cm. In one embodiment the second solution with an increased pH value has a pH of about 2.7 to about 2.9 and has a conductivity value of about 19 mS/cm.

In one embodiment the second solution with an increased pH value has a pH of about 2.7 to about 3.0 and has a conductivity value of about 17 mS/cm to about 19 mS/cm. In one preferred embodiment the second solution with an increased pH value has a pH of about 2.7 to about 2.9 and has a conductivity value of about 17 mS/cm to about 19 mS/cm.

It is understood in the art, that pH and conductivity are related to each other. Therefore, the pH values of the wash solutions can be different to those described above, if also the conductivity is changed. For example, the pH can be increased to a higher extent when the conductivity is lower, while achieving comparable purification results.

It has been found that when applying the solution with increased pH value, the conductivity should be kept constant with respect to the first washing solution. In one embodiment the second solution with an increased pH value and the first solution with a pH of about 2.4 to about 2.7 have about the same, constant conductivity value.

After the poly-PEGylated erythropoietin has been recovered from the chromatography material the elution of the mono-PEGylated erythropoietin by an increase in conductivity is started. The conductivity of the mobile phase passing the chromatography material is increased linearly or step-wise.

In one embodiment the solution with increasing conductivity has a conductivity that increases linearly or step-wise.

In the conductivity gradient at first mono-PEGylated erythropoietin is recovered from the column and afterwards substantially homogeneous non-PEGylated erythropoietin is recovered.

The increase in the conductivity is in one embodiment by applying a solution with an increasing sodium chloride concentration. In one embodiment the solution applied to increase the conductivity has a pH value of from pH 2.5 to pH 3.5.

In one embodiment the solution comprising a mixture of free erythropoietin and free poly (ethylene glycol) as well as fusion proteins (i.e. protein conjugates) of erythropoietin and poly (ethylene glycol) with one or more poly (ethylene glycol) residues per erythropoietin molecule is applied to the chromatography material that of from 1 mg/ml up to 4 mg/ml protein is applied to 1 ml of chromatography material.

It has been found that method as reported herein (especially when using Toyopearl® SP-650 as chromatography material) can be used for purification of protein in large scale.

In one embodiment the method is used in large scale protein preparations wherein the chromatography column of step a) has a diameter of at least 30 cm.

The term "Toyopearl® SP-650 chromatography material" denotes a cation exchange chromatography material (available from Tosoh Corporation). The Toyopearl® SP-650 chromatography material has a matrix of methacrylate with a sulfopropyl as functional group and is, thus, a strong cation exchange chromatography material. The Toyopearl® SP-650 M chromatography material has a particle size of 65 µm.

In one embodiment the cation exchange chromatography material has a matrix of methacrylate. In one embodiment the cation exchange chromatography material has a sulfopropyl as functional group. In one embodiment the cation exchange chromatography material has a matrix of methacrylate with a sulfopropyl as functional group. In one embodiment the cation exchange chromatography material has a particle size of about 65 µm.

The following examples, sequence listing and figures are provided to aid the understanding of the present invention, the true scope of which is set forth in the appended claims. It is understood that modifications can be made in the procedures set forth without departing from the spirit of the invention.

DESCRIPTION OF THE SEQUENCE LISTING

SEQ ID NO: 01 Amino acid sequence of human erythropoietin.
SEQ ID NO: 02 Amino acid sequence of human erythropoietin.

EXAMPLE 1

Chromatography of a PEGylated Erythropoietin Preparation with a Toyopearl® SP-650 M Chromatography Material without an Additional Wash Step (pH 2.5)

Figure 1:
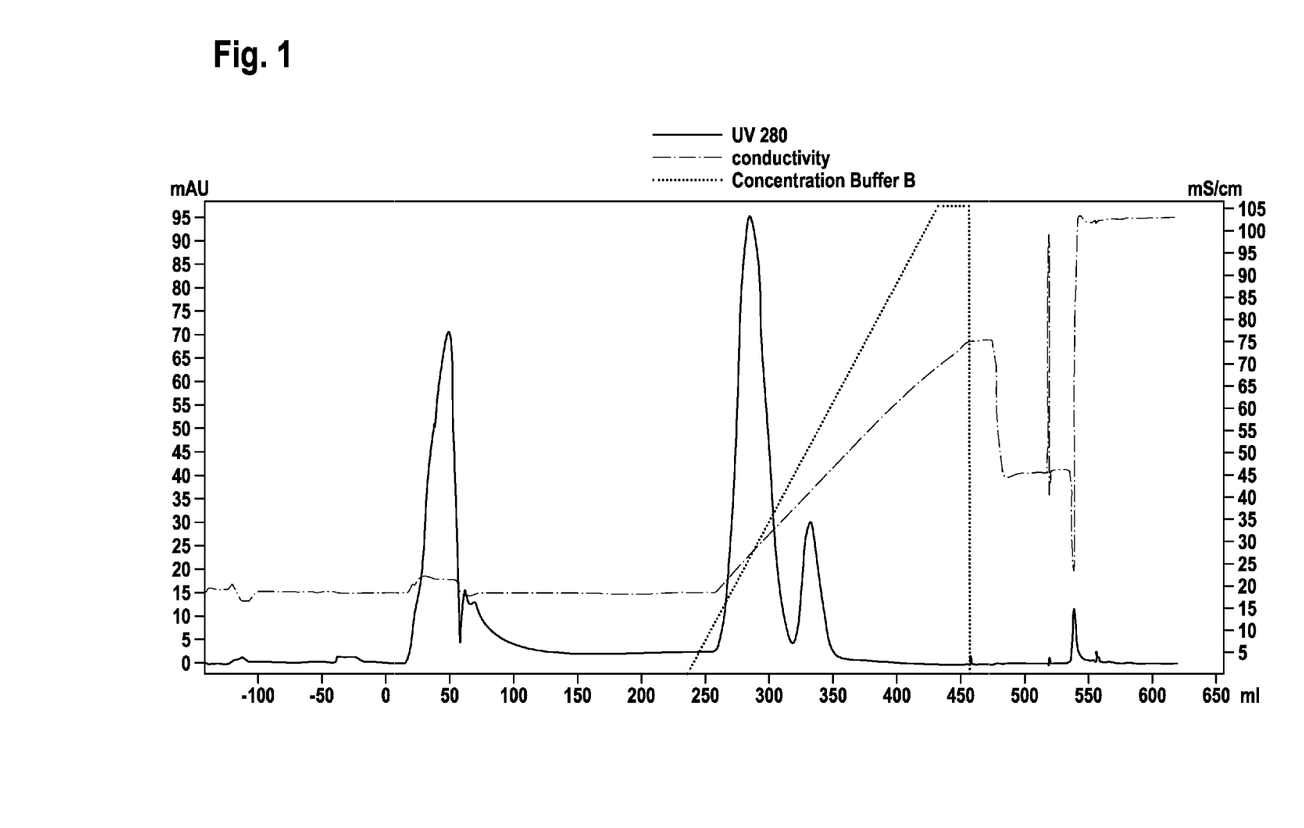
FIG. 1 Elution chromatogram of a purification of a PEGylated erythropoietin preparation with a method as reported in Example 1 (wash at pH 2.5; no additional wash step).

The PEGylated Erythropoietin Chromatography was performed as shown below.
PEGylated Erythropoietin Chromatography:
resin: SP Toyopearl 650 M
bed volume: 19.6 ml
sample loading: 1.3 mg/ml resin
flow rate: 1.3 ml/min
solutions: A: 100 mM potassium phosphate, 100 mM sodium chloride, adjusted to pH 2.5, adjusted to LF=19 mS/cm with 5 m sodium chloride
    B: 100 mM potassium phosphate, 375 mM sodium chloride, adjusted to pH 2.5
application solution: 100% A
wash solution: 100% A
wash volume: 100 ml (5 column volumes (CV))
wash solution (wash 2): none
wash volume (wash 2): none
linear gradient elution solution: 100% B
linear gradient: within 196 ml (10 column volumes) to 100% B
wavelength: 280 nm
The elution chromatogram for this method is shown in FIG. 1.

EXAMPLE 2

Chromatography of a PEGylated Erythropoietin Preparation with a Toyopearl® SP-650 M Chromatography Material without an Additional Wash Step (pH 3.0)

Figure 4:
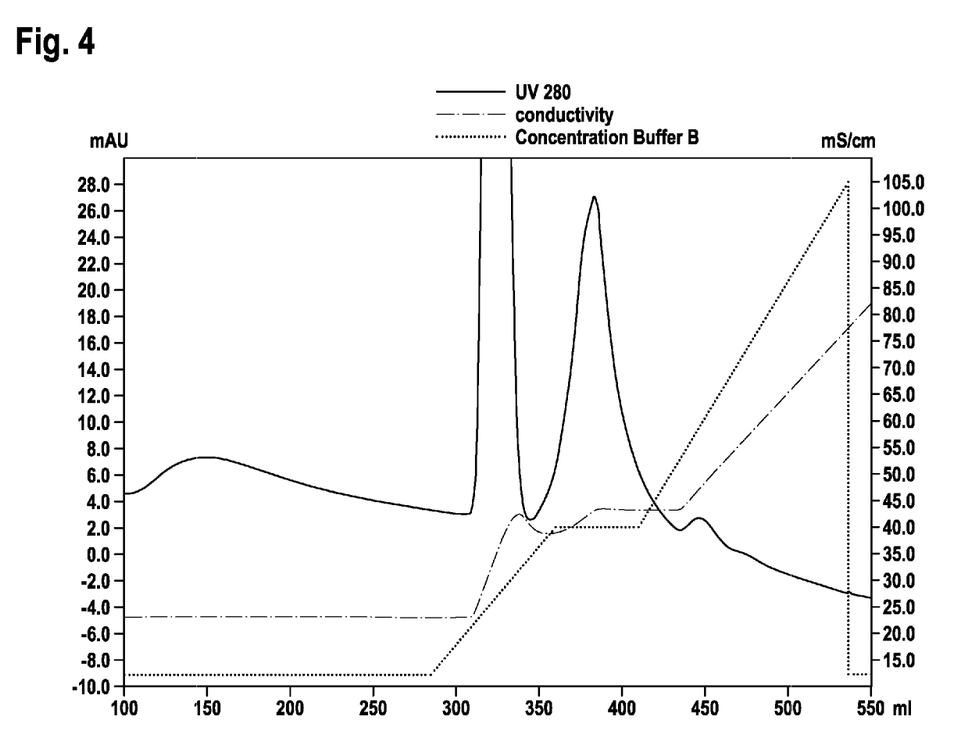
FIG. 4 Elution chromatogram of a purification of a PEGylated erythropoietin preparation with a method as reported in Example 2 (wash at pH 3.0; no additional wash step).

The PEGylated Erythropoietin Chromatography was performed as shown below.
PEGylated Erythropoietin Chromatography:
resin: SP Toyopearl 650 M
bed volume: 19.6 ml
sample loading: 1.3 mg/ml resin
flow rate: 1.3 ml/min
solutions: A: 100 mM potassium phosphate, 100 mM sodium chloride, adjusted to pH 3.0, with a conductivity value=20.5 mS/cm
    B: 100 mM potassium phosphate, 375 mM sodium chloride, adjusted to pH 2.5
application solution: 100% A
wash solution: 100% A
wash volume: 100 ml (5 column volumes (CV))
wash solution (wash 2): none
wash volume (wash 2): none
linear gradient elution solution: 100% B
linear gradient: within 196 ml (10 column volumes) to 100% B
wavelength: 280 nm
The elution chromatogram for this method is shown in FIG. 4.

EXAMPLE 3

Figure 2:
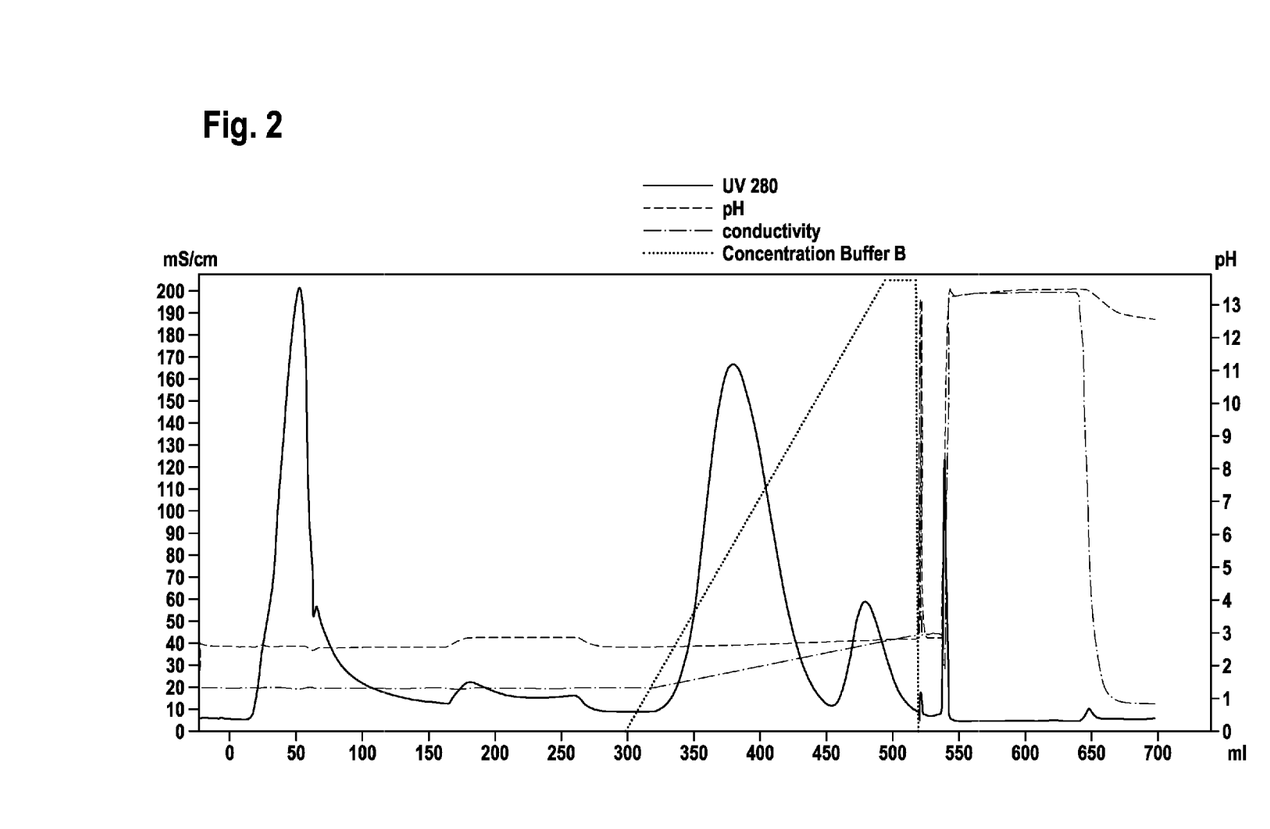
FIG. 2 Elution chromatogram of a purification of a PEGylated erythropoietin preparation with a method as reported in Example 3 (wash at pH 2.5; additional wash step at pH 2.8).
Figure 3:
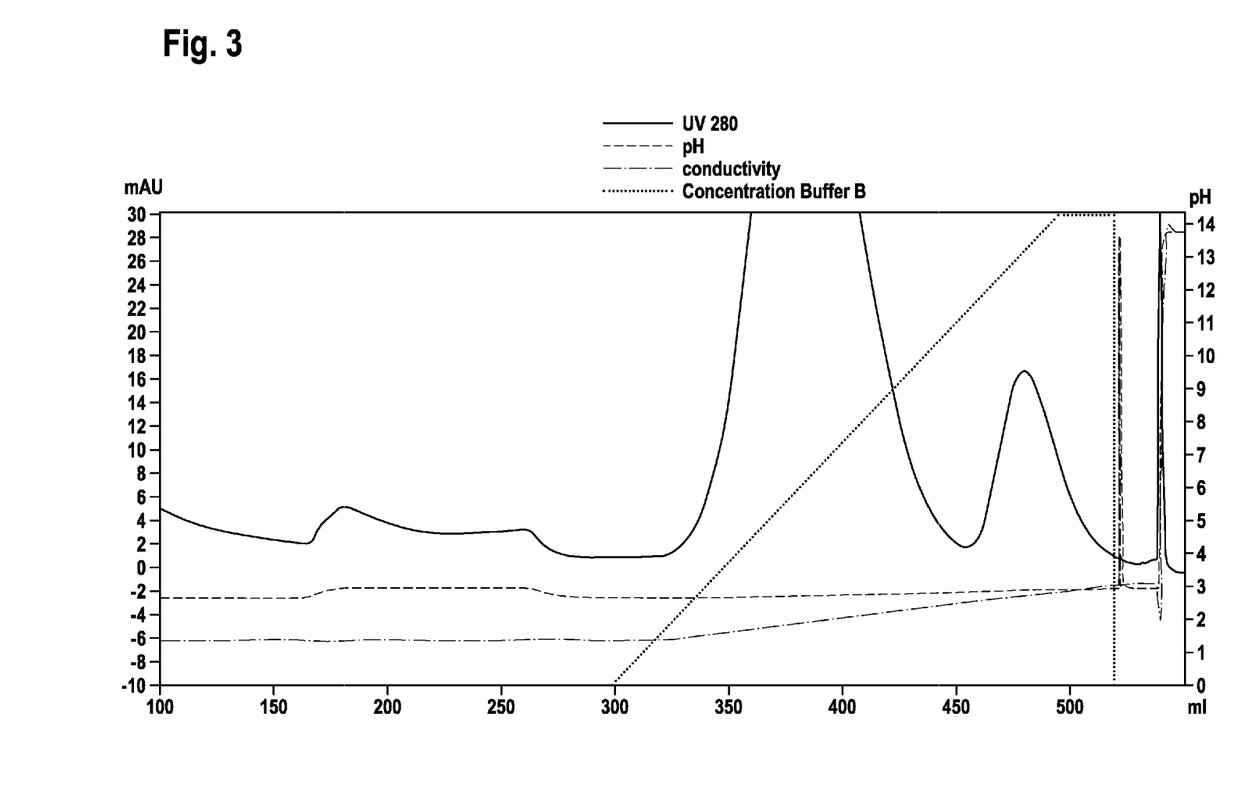
FIG. 3 Magnification of the elution chromatogram (FIG. 2) of a purification of a PEGylated erythropoietin preparation with a method as reported in Example 3 (wash at pH 2.5; additional wash step at pH 2.8).

Chromatography of a PEGylated Erythropoietin Preparation with a Toyopearl® SP-650 M Chromatography Material with an Additional Wash Step with a Solution with a pH of 2.8 and a Conductivity of about 19 mS/Cm The PEGylated Erythropoietin Chromatography was performed as shown below:
resin: SP Toyopearl 650 M
bed volume: 19.6 ml
sample loading: 1.3 mg/ml resin
flow rate: 1.3 ml/min
solutions: A: 100 mM potassium phosphate, 100 mM sodium chloride, adjusted to pH 2.5, adjusted to LF=19 mS/cm with 5 m sodium chloride
    B: 100 mM potassium phosphate, 375 mM sodium chloride, adjusted to pH 2.5
    Additional wash (wash 2): 100 mM potassium phosphate, 100 mM sodium chloride, adjusted to pH 2.8, adjusted to LF=19 mS/cm with water
application solution: 100% A
wash solution: 100% A
wash volume: 100 ml (5 column volumes (CV))
wash solution (wash 2): 100% Additional wash (wash 2)
wash volume (wash 2): 100 ml (5 column volumes (CV))
wash solution (wash 3): 100% A
wash volume (wash 3): 60 ml (3 column volumes (CV))
linear gradient elution solution: 100% B
linear gradient: within 196 ml (10 column volumes) to 100% B
wavelength: 280 nm
The elution chromatogram for this method is shown in FIG. 2 and a magnification is shown in FIG. 3.

EXAMPLE 4

Figure 5:
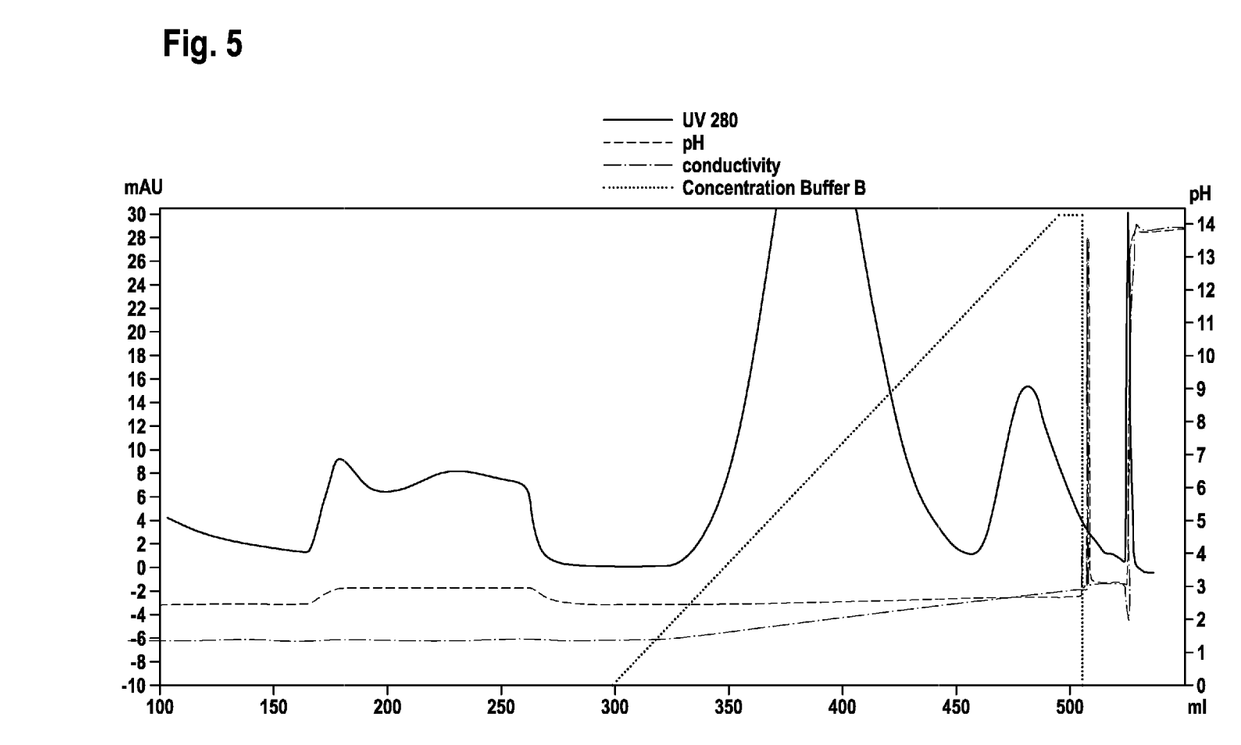
FIG. 5 Elution chromatogram of a purification of a PEGylated erythropoietin preparation with a method as reported in Example 4 (wash at pH 2.5; additional wash step at pH 3.0).

Chromatography of a PEGylated Erythropoietin Preparation with a Toyopearl® SP-650 M Chromatography Material with an Additional Wash Step with a Solution with a pH of 3.0 and a Conductivity of about 19 mS/Cm The PEGylated Erythropoietin Chromatography was performed as shown below:
resin: SP Toyopearl 650 M
bed volume: 19.6 ml
sample loading: 1.3 mg/ml resin flow rate: 1.3 ml/min
solutions: A: 100 mM potassium phosphate, 100 mM sodium chloride, adjusted to pH 2.5, adjusted to LF=19 mS/cm with 5 m sodium chloride
B: 100 mM potassium phosphate, 375 mM sodium chloride, adjusted to pH 2.5
Additional wash (wash 2): 100 mM potassium phosphate, 100 mM sodium chloride, adjusted to pH 3.0, adjusted to LF=19 mS/cm with water
application solution: 100% A
wash solution: 100% A
wash volume: 100 ml (5 column volumes (CV))
wash solution (wash 2): 100% Additional wash (wash 2)
wash volume (wash 2): 100 ml (5 column volumes (CV))
wash solution (wash 3): 100% A
wash volume (wash 3): 60 ml (3 column volumes (CV))
linear gradient elution solution: 100% B
linear gradient: within 196 ml (10 column volumes) to 100% B
wavelength: 280 nm The elution chromatogram for this method is shown in FIG. 5.

EXAMPLE 5

Chromatography of a PEGylated Erythropoietin Preparation with a Toyopearl® SP-650 M Chromatography Material with an Additional Wash Step with a Solution of Different pH Values (pH 2.8, 2.9 or 3.0) and a Conductivity of about 17 mS/Cm The PEGylated Erythropoietin Chromatography was performed as shown below:
resin: SP Toyopearl 650 M
bed volume: 19.2 ml
sample loading: 0.7 mg/ml resin
flow rate: 150 cm/h
solutions: A: 100 mM potassium phosphate, 100 mM sodium chloride, adjusted to pH 2.5, adjusted to LF=17 mS/cm with 5 m sodium chloride
B: 100 mM potassium phosphate, 375 mM sodium chloride, adjusted to pH 2.5
Additional wash (wash 2): 100 mM potassium phosphate, 100 mM sodium chloride, adjusted to pH 2.8, 2.9 or 3.0, adjusted to LF=17 mS/cm with water
application solution: 100% A
wash solution: 100% A
wash volume: 96.2 ml (5 column volumes (CV))
wash solution (wash 2): 100% Additional wash (wash 2)
wash volume (wash 2): 96.2 ml (5 column volumes (CV))
wash solution (wash 3): 100% A
wash volume (wash 3): 57.7 ml (3 column volumes (CV))
linear gradient elution solution: 100% B
linear gradient: within 192 ml (10 column volumes) to 100% B
wavelength: 280 nm
The results are shown below:

|  | Wash 2 (additional wash) pH 2.8, 17 mS/cm | Wash 2 (additional wash) pH 2.9, 17 mS/cm | Wash 2 (additional wash) pH 3.0, 17 mS/cm |
| --- | --- | --- | --- |
| Purity Pool MonoPEG EPO [%] | 98.81 | 99.50 | 99.72 |
| Yield MonoPEG EPO [%] | 98.11 | 95.40 | 82.81 |

Yields are calculated based on the monoPEGylated EPO content in the starting material.

EXAMPLE 6

Chromatography of a PEGylated Erythropoietin Preparation with a Toyopearl® SP-650 M Chromatography Material with an Additional Wash Step with a Solution of Different pH Values (pH 2.8, 2.9 or 3.0) and a Conductivity of about 18 mS/cm The PEGylated Erythropoietin Chromatography was performed as shown below:
resin: SP Toyopearl 650 M
bed volume: 19.2 ml
sample loading: 0.7 mg/ml resin
flow rate: 150 cm/h
solutions: A: 100 mM potassium phosphate, 100 mM sodium chloride, adjusted to pH 2.5, adjusted to LF=18 mS/cm with 5 m sodium chloride
B: 100 mM potassium phosphate, 375 mM sodium chloride, adjusted to pH 2.5
Additional wash (wash 2): 100 mM potassium phosphate, 100 mM sodium chloride, adjusted to pH 2.8, 2.9 or 3.0, adjusted to LF=18 mS/cm with water
application solution: 100% A
wash solution: 100% A
wash volume: 96.2 ml (5 column volumes (CV))
wash solution (wash 2): 100% Additional wash (wash 2)
wash volume (wash 2): 96.2 ml (5 column volumes (CV))
wash solution (wash 3): 100% A
wash volume (wash 3): 57.7 ml (3 column volumes (CV))
linear gradient elution solution: 100% B
linear gradient: within 192 ml (10 column volumes) to 100%
wavelength: 280 nm
The results are shown below:

|  | Wash 2 (additional wash) pH 2.8, 18 mS/cm | Wash 2 (additional wash) pH 2.9, 18 mS/cm | Wash 2 (additional wash) pH 3.0, 18 mS/cm |
| --- | --- | --- | --- |
| Purity Pool MonoPEG EPO [%] | 99.54 | 100 | 99.24 |
| Yield MonoPEG EPO [%] | 78.60 | 81.82 | 64.11 |

Yields are calculated based on the monoPEGylated EPO content in the starting material.

EXAMPLE 7

Chromatography of a PEGylated Erythropoietin Preparation with a Toyopearl® SP-650 M Chromatography Material with an Additional Wash Step with a Solution of Different pH Values (pH 2.8, 2.9 or 3.0) and a Conductivity of About 19 mS/cm The PEGylated Erythropoietin Chromatography was performed as shown below:
resin: SP Toyopearl 650 M
bed volume: 19.2 ml
sample loading: 0.7 mg/ml resin
flow rate: 150 cm/h
solutions: A: 100 mM potassium phosphate, 100 mM sodium chloride, adjusted to pH 2.5, adjusted to LF=19 mS/cm with 5 m sodium chloride
    B: 100 mM potassium phosphate, 375 mM sodium chloride, adjusted to pH 2.5
    Additional wash (wash 2): 100 mM potassium phosphate, 100 mM sodium chloride, adjusted to pH 2.8, 2.9 or 3.0, adjusted to LF=19 mS/cm with water
application solution: 100% A
wash solution: 100% A
wash volume: 96.2 ml (5 column volumes (CV))
wash solution (wash 2): 100% Additional wash (wash 2)
wash volume (wash 2): 96.2 ml (5 column volumes (CV))
wash solution (wash 3): 100% A
wash volume (wash 3): 57.7 ml (3 column volumes (CV))
linear gradient elution solution: 100% B linear gradient: within 196 ml (10 column volumes) to 100% B
wavelength: 280 nm
The results are shown below:

|  | Wash 2 (additional wash) pH 2.8, 19 mS/cm | Wash 2 (additional wash) pH 2.9, 19 mS/cm | Wash 2 (additional wash) pH 3.0, 19 mS/cm |
|---|---|---|---|
| Purity Pool MonoPEG EPO [%] | 100 | 100 | 100 |
| Yield MonoPEG EPO [%] | 65.57 | 59.06 | 45.02 |

Yields are calculated based on the monoPEGylated EPO content in the starting material.

The invention claimed is:

1. A method for purifying a protein, which comprises erythropoietin and a single poly (ethylene glycol) residue, comprising the following steps:
   a) applying a solution comprising a mixture of erythropoietin and conjugates of erythropoietin and poly (ethylene glycol) with one or more poly (ethylene glycol) residues per erythropoietin molecule to a column, comprising a chromatography material that has a matrix of methacrylate with a sulfopropyl as functional group, to which a first solution with a pH of about 2.4 to about 2.7 has been applied,
   b) applying a second solution with an increased pH value with respect to the first solution,
   c) applying a solution with increased or increasing conductivity to the column and thereby recovering the protein, which comprises erythropoietin and a single poly (ethylene glycol) residue,
wherein the second solution with an increased pH value has a pH of about 2.7 to about 3.0 and has a conductivity value of about 17 mS/cm to about 19 mS/cm.

2. The method according to claim 1, characterized in that the method further comprises the step of re-applying the first solution with a pH of about 2.4 to about 2.7 after step b) and before step c).

3. The method according to claim 1, characterized in that the second solution with an increased pH value is a solution with a constant conductivity value.

4. The method according to claim 1, characterized in that the second solution with an increased pH value and the first solution with a pH of about 2.4 to about 2.7 have about the same constant conductivity value.

5. The method according to claim 1, characterized in that the second solution with an increased pH value and/or the first solution with a pH of about 2.4 to about 2.7 have a constant conductivity value of about 17 mS/cm to about 19 mS/cm.

6. The method according to claim 1, characterized in that the solution comprising a mixture of erythropoietin and conjugates of erythropoietin and poly (ethylene glycol) with one or more poly (ethylene glycol) residues per erythropoietin molecule is not adjusted to a conductivity value of about 19 mS/cm.

7. The method according to claim 1, characterized in that the solution with increasing conductivity is a solution with increasing sodium chloride concentration.

8. The method according to claim 1, characterized in that the solution with increasing conductivity has a conductivity that increases linearly or step-wise.

9. The method according to claim 1, characterized in that the method is used in large scale protein preparations wherein the chromatography column of step a) has a diameter of at least 30 cm.

10. The method according to claim 1, characterized in that the erythropoietin is human erythropoietin.

11. The method according to claim 10, characterized in that the human erythropoietin has the amino acid sequence of SEQ ID NO: 01 or SEQ ID NO: 02.

12. The method according to claim 1, characterized in that the single poly (ethylene glycol) residue has a molecular weight of from 20 kDa to 40 kDa.

* * * * *